United States Patent [19]
Atkinson et al.

[11] Patent Number: 6,075,252
[45] Date of Patent: Jun. 13, 2000

[54] CONTAMINANT IDENTIFICATION AND CONCENTRATION DETERMINATION BY MONITORING THE TEMPORAL CHARACTERISTICS OF AN INTRACAVITY LASER

[75] Inventors: George H. Atkinson; Jeffrey S. Pilgrim, both of Tucson, Ariz.

[73] Assignee: Innovative Lasers Corporation, Tucson, Ariz.

[21] Appl. No.: 09/192,744

[22] Filed: Nov. 16, 1998

[51] Int. Cl.[7] .................................................. G01N 21/86
[52] U.S. Cl. .................................. 250/559.4; 250/339.13
[58] Field of Search ................................. 250/559.4, 343, 250/346, 339.12, 339.13; 356/347, 432, 437, 436

[56] References Cited

U.S. PATENT DOCUMENTS

5,815,277  9/1998  Zare et al. ............................... 356/440

*Primary Examiner*—Que T. Le
*Attorney, Agent, or Firm*—Benman & Collins

[57] ABSTRACT

A method and apparatus for detecting the presence of a specific concentration of gaseous species within a calibrated range in a gas sample are disclosed. The ILS gas detection system of the present invention simply comprises an ILS laser and an optical detector. However, the spectral bandwidth of the ILS laser is preferably entirely included within one of the absorption bands or regions assigned to the intracavity gaseous species being monitored. Thus, within the calibrated range, the presence of the gaseous species changes the temporal characteristics of the ILS laser. Consequently, only a temporal characteristic of the output of the ILS laser need be monitored in order to quantitatively determine the concentration of the absorbing gaseous species when using the ILS method of the present invention.

24 Claims, 6 Drawing Sheets

CONTAMINANT IDENTIFICATION AND CONCENTRATION DETERMINATION BY MONITORING THE TEMPORAL CHARACTERISTICS OF AN INTRACAVITY LASER

CROSS-REFERENCE TO RELATED APPLICATION

This application is related to applications Ser. No. 09/165,884, now U.S. Pat. No. 5,991,032 and 09/166,003, now U.S. Pat. No. 5,999,259, both filed on Oct. 2, 1998. The former application is directed to the use of an ILS laser without any wavelength-selective element(s) whereby the total laser output intensity is used to determine gaseous species concentrations. The latter application concerns a method for detecting the presence of a specific concentration of gaseous species in a gas sample using an ILS laser with a wavelength-selective element for measuring changes in the spectral output of the sensor. The present application is directed to the detection of altered temporal characteristics of the ILS laser in the presence of a gaseous species to determine its concentration.

TECHNICAL FIELD

This invention relates, generally, to the detection of contaminants in gases, and more particularly, to the high sensitivity detection of gaseous molecules, atoms, radicals, and/or ions by laser techniques generally termed intracavity laser spectroscopy.

BACKGROUND OF THE INVENTION

A laser in its simplest form can be schematically illustrated as including a gain medium that is located between two mirrors. Light within the laser cavity is reflected back and forth between the mirrors, each time passing through the gain medium, which produces optical gain. The mirror coating on the first mirror may be totally reflective, while the mirror coating on the second mirror may be partially reflective, thereby permitting some light to escape from the laser cavity. The spatial region between the reflective surfaces of the mirrors defines the laser resonator or cavity, and in the context of the present invention relates to the so-called "intracavity region".

The intensity of the laser output is a function of both the wavelength region over which the gain medium operates and the reflectivity of the resonator elements. Normally this output is broad and without sharp, distinctive spectral features.

The identification of gaseous species, e.g., atoms, molecules, radicals, or ions, via laser spectroscopy requires that the laser output be in a wavelength region where the species absorbs. In conventional applications of lasers to the detection of gaseous species, laser radiation is used to excite a gas sample that is external to the laser in order to produce a secondary signal such as ionization or fluorescence. Alternatively, in conventional absorption spectroscopy, laser light is passed through a gas sample that is situated outside of the laser and attenuation that varies with wavelength is monitored.

Some twenty years ago, another detection methodology, intracavity laser spectroscopy (ILS) was first explored; see, e.g., G. Atkinson et al, "Detection of Free Radicals by an Intracavity Dye Laser Technique", *Journal Of Chemical Physics*, Vol. 59, pp. 350–354, (Jul. 1, 1973). In ILS, a laser itself is used as the detector. The gas sample to be analyzed is inserted into the optical cavity of a multimode, homogeneously broadened laser. Atkinson et al, supra, showed that by placing gaseous molecules, atoms, radicals, and/or ions in either their ground or excited states inside the optical cavity, the laser output can be altered. In particular, the absorption spectrum of the intracavity species appears in the spectral output of the laser.

Distinct absorption features in the laser output arise from the intracavity losses introduced by the gaseous species that are absorbing. (As used herein, an absorption feature corresponds to a series of consecutive wavelengths where the light intensity reaches a single local minimum in light intensity in a plot of light intensity versus wavelength.) In a multimode laser, intracavity absorption losses compete with the laser gain via the normal mode dynamics. As a result, attenuation can be observed in the laser output intensity at wavelengths where the stronger intracavity absorption features compete effectively against the gain of the laser. The more intense the absorption features, the larger the decrease in the laser output intensity at those wavelengths.

By inserting the absorbing gaseous species inside the laser resonator, ILS can provide a detection sensitivity that is enhanced over conventional spectroscopy methods. The enhanced detection sensitivity of ILS techniques derives from the non-linear competition between (1) the gain produced in the laser gain medium and (2) the absorber loss(es). As a result, ILS can be utilized to detect both weak absorption and/or extremely small absorber concentrations.

Each gaseous species in the optical cavity can be uniquely identified by its respective absorption spectrum or signature. Additionally, the intensity of a specific absorption feature or features in the spectral signature can be used to determine the concentration of the gaseous species once the sensor is appropriately calibrated. (As used herein, the term "spectral signature" corresponds to the wavelength plotted against absorption intensity or absorbance that uniquely identifies the gaseous species.)

The spectral signature of the gaseous species can be obtained by dispersing the output of the ILS laser with respect to wavelength. Two detection schemes are typically employed to disperse the output of the ILS laser and thereby obtain the spectral signature of the gaseous species. The output of the ILS laser can be passed through a fixed-wavelength, dispersive spectrometer, and the specific spectral region that is resolved by this spectrometer can be recorded using a multichannel detector; see U.S. Pat. No. 5,747,807, issued May 5, 1998, to G. H. Atkinson et al entitled "Diode Laser-Pumped Laser System for Ultrasensitive Gas Detection via Intracavity Laser Spectroscopy (ILS)". Alternatively, a spectrometer that can be scanned in wavelength can be employed to selectively resolve different spectral regions that are recorded with a single channel detector, supra.

Prior art ILS detection systems employ ILS lasers having a spectral bandwidth that is substantially broad relative to the bandwidth of the absorption features in the absorption spectrum of the intracavity species to be detected; see U.S. Pat. No. 5,689,334, issued Nov. 18, 1997, to G. H. Atkinson et al entitled "Intracavity Laser Spectroscope for High Sensitivity Detection of Contaminants". In particular, the laser systems possess an operational wavelength bandwidth that is at least three times as broad as the absorption features of the gaseous species being monitored.

Prior art methods of performing ILS, however, while successfully demonstrated in the laboratory, are too large and complex for many commercial applications. In particular, the requirement for a spectrometer to disperse the spectral output of the laser, as well as for a computer to analyze the absorption features, adds to the size and complexity of the detection system. In contrast, the constraints of commercial reality dictate that a gas detector be conveniently sized, relatively inexpensive, and reliable.

One approach used to measure contaminant concentration based on temporal characteristics is called "cavity ringdown". Such a technique allows optical absorption measurements to be made using a pulsed light source and offers a sensitivity that is greater than that attained using stabilized continuous light sources. The technique is based upon the measurement of the rate of absorption rather than the magnitude of absorption of a light pulse confined within a closed optical cavity. Examples of cavity ringdown are described, for example, in A. O'Keefe et al, "Cavity ringdown optical spectrometer for absorption measurements using pulsed laser sources", *Reviews of Scientific Instruments*, Vol. 59, No. 12, pp. 2544–2551 (December 1988); J. J. Scherer et al, "Cavity Ringdown Laser Absorption Spectroscopy: History, Development, and Application to Pulsed Molecular Beams", *Chemical Reviews*, Vol. 97, No. 1, pp. 25–52 (Feb. 5, 1997); U.S. Pat. No. 5,528,040, issued Jun. 18, 1996, to K. K. Lehman; and U.S. Pat. No. 5,815,277, issued Sep. 29, 1998, to R. N. Zare et al.

Cavity ringdown laser absorption spectroscopy is a well-known and successfully utilized technique for detecting trace contaminants in the gas phase. It differs, however, in several respects from the method of the present invention. (1) Cavity ringdown is implemented in a passive optical resonator, i.e. there is not an active optical element such as a gain medium. In contrast, the present invention relates to measurement and characterization of temporal phenomena inside an active optical resonator, specifically, a laser resonator. (2) The photon pulses exiting a cavity ringdown resonator are spaced periodically by the round trip time of the laser pulse injected into the passive resonator. In contrast, the temporal phenomena of the present invention may or may not include photon pulses at all. In the event that photon pulses are produced and measured, they would not be spaced by the cavity round trip time except as a coincidence. (3) The photon pulses exiting a cavity ringdown resonator decay towards zero output intensity. In contrast, in the event that photon pulses are produced in the present invention, they decay to a steady-state non-zero output intensity given by the continuous wave (cw) output power of the laser. (4) In cavity ringdown, the presence of an absorber does not change the period of the photon pulses exiting the passive resonator, as this is determined by the round trip time determined by the speed of light and the cavity length. In contrast, the presence of an absorber in the present invention may, and usually does, change the period of photon pulses exiting the active resonator.

Thus, there remains a need for a methodology that significantly reduces (1) the complexity of ILS measurements and (2) the size of ILS instrumentation, for example, by eliminating the need for a spectrometer and a computer.

SUMMARY OF THE INVENTION

In accordance with the present invention, a method for detecting the presence of a specific concentration of a gaseous species in a gas sample within a calibrated range employing an ILS laser is disclosed. The method comprises:

(a) determining that the ILS laser has at least one measurable temporal characteristic where the gaseous species absorbs light and the absorption induced by the gaseous species is large enough to measurably change the temporal characteristics of the laser within the calibrated range.

(b) providing the ILS laser comprising:
  (i) a laser cavity; and
  (ii) a gain medium,
  wherein the ILS laser has at least one measurable temporal characteristic;

(c) situating the gain medium such that an output beam from the gain medium is directed through the gas sample that is contained in the laser cavity prior to exiting the laser cavity; and (d) situating a detector having a temporal bandwidth sufficient to detect at least one temporal characteristic so as to detect the change in the temporal characteristic of the laser.

Additionally, a gas detection system for detecting the presence of a specific concentration within the calibrated range of a gaseous species in a gas sample, is provided wherein the gaseous species absorbs light within at least one single band of consecutive wavelengths and thereby changes the temporal characteristics of the output of the ILS laser by a specific amount. The gas detection system comprises:

(a) an ILS laser comprising:
  (i) a laser cavity; and
  (ii) a gain medium,
  the ILS laser having at least one measurable temporal characteristic when operating in a wavelength region where the gaseous species is absorbing and the absorption induced by the gaseous species is large enough to measurably change the temporal characteristic(s) of the laser within a calibrated range;

(b) a container for containing the gas sample in the laser cavity, the container allowing an output beam emanating from the gain medium to pass through the gas sample prior to exiting the laser cavity; and (c) a detector having a temporal bandwidth sufficient to measure the temporal characteristic(s).

In accordance with the present invention, the present inventors have devised a commercially-viable contaminant sensor system that is smaller, simpler, and less expensive to construct than any ILS laser system disclosed in prior art.

Other objects, features, and advantages of the present invention will become apparent upon consideration of the following detailed description and accompanying drawings, in which like reference designations represent like features throughout the Figures.

BRIEF DESCRIPTION OF THE DRAWINGS

The drawings referred to in this description should be understood as not being drawn to scale except if specifically noted.

DESCRIPTION OF PREFERRED EMBODIMENTS

Reference is now made in detail to a specific embodiment of the present invention, which illustrates the best mode presently contemplated by the inventors for practicing the invention. Alternative embodiments are also briefly described as applicable.

The present invention is directed to extremely high sensitivity detection of gaseous species using an ILS sensor. The term "gaseous species" as used herein refers to molecular, atomic, radical, and/or ionic species that may be present in gaseous materials such as those that are used in the fabrication of silicon films. Accordingly, the ILS gas detection system of the present invention may be used to detect the presence of a contaminant (e.g., water) in a gaseous material (e.g., nitrogen). Alternatively, ILS detection may be used to determine if a gas line (e.g., nitrogen gas line) has been sufficiently purged of the gaseous material (i.e., water).

Figure 1A:
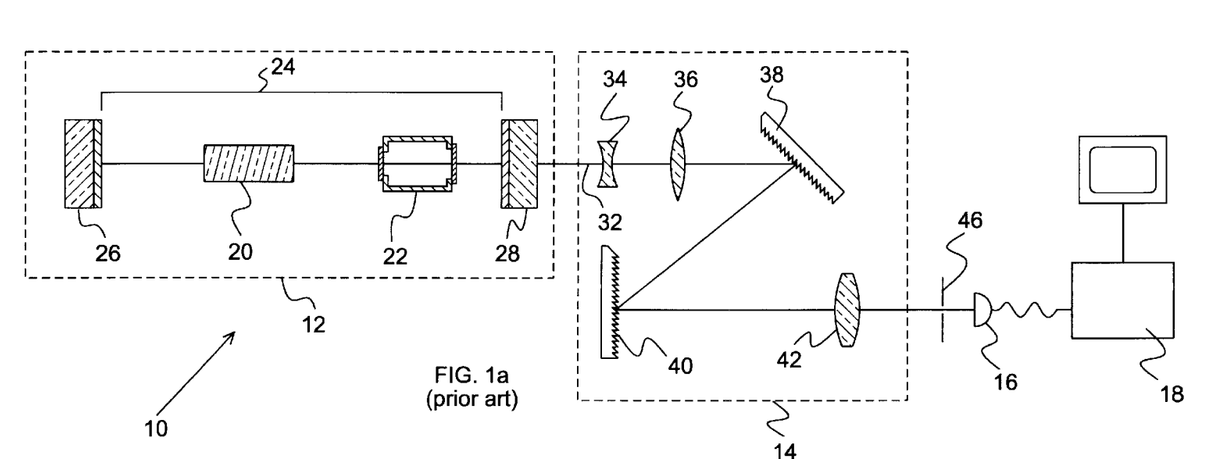
FIG. 1a is a cross-sectional view depicting a prior art gas detection system comprising an ILS laser, a spectrometer assembly, an optical detector, and a computer for analyzing electrical output from the optical detector.
Figure 1B:
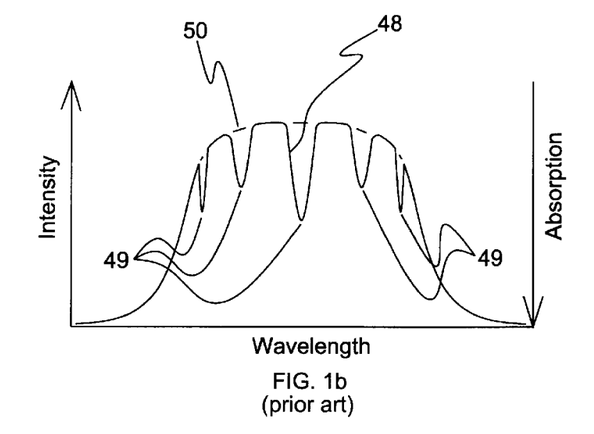
FIG. 1b, on coordinates of intensity and wavelength, is a plot of the spectrally resolved output of the prior art ILS laser both (i) when absorbing gaseous species are present in the laser cavity and (ii) when the absorbing gaseous species are not present within the laser cavity.

FIGS. 1a and 1b schematically illustrate the prior art method of performing ILS detection. Specifically, in FIG. 1a, a cross-section of an ILS gas detection system is shown comprising an ILS laser 12, a spectrometer assembly 14, an optical detector 16, and a computer 18 for analyzing electrical output from the optical detector.

The ILS laser 12 depicted in FIG. 1a includes a gain medium 20 and a gas sample cell 22 that are situated within an optical resonator 24 defined by the entire optical path length between mirrors 26 and 28. It will be appreciated that the ILS laser 12 additionally requires a pumping source (not shown), such as an optical pumping source that delivers optical radiation to the gain medium 20 to thereby drive the ILS laser 12.

FIG. 1a shows that laser light generated within the gain medium 20 is directed to the gas sample cell 22 and passes through the gas sample therein. As described above, gaseous species within the optical resonator or laser cavity 24 and, in particular, within the gas sample cell 22, may introduce absorption losses if absorption features are located in the wavelength region where the ILS laser 12 operates. Accordingly, the output beam 32 of the ILS laser 12 can be analyzed to identify the presence of an absorbing gaseous species within the laser cavity 24 by determining if the output beam exiting the ILS laser contains absorption features identical to those in the spectral signature of the gaseous species. It will be noted that the spectral signature contains information on intensity and wavelength.

As used herein, an absorption feature corresponds to an absorption line, i.e., a region of consecutive wavelengths observable in a plot of light intensity versus wavelength that includes and surrounds a single local minimum in light intensity (i.e., where absorption reaches a maximum). Each absorption line has a finite bandwidth and a point where the absorption reaches a maximum (or the output intensity reaches a minimum). With respect to the present invention, absorption features are important because all the wavelengths that make up the absorbing feature are wavelengths where the gaseous species is absorbing.

Additionally, as used herein, the term "absorption band" is defined as a single uninterrupted wavelength region in the absorption spectrum wherein absorption occurs at each wavelength. Accordingly, if an absorption spectrum contains two absorption lines, $A_1$ and $A_2$, separated by region, B, where no absorption is observed, then two absorbing lines, $A_1$ and $A_2$, correspond to separate absorption bands. If, however, the two absorption lines $A_1$ and $A_2$, are only separated by a local absorption minimum (or local maximum in intensity), then the two absorbing lines, $A_1$ and $A_2$, correspond to a single absorption band. For example, absorption lines that are separate and distinct at a first concentration, may at a second, higher concentration, come together and coalesces to form a single absorption band. It will be appreciated that the temperature, the generation time, and the pumping power will also affect the output spectrum and the measured absorption spectrum. Accordingly, the number of absorbing bands in a measured absorption spectrum will also vary with temperature, generation time, and pumping power.

The number of absorption bands detected also depends on the concentration of the absorbing intracavity species.

To analyze the spectral output of the ILS laser 12, the ILS output beam 32 from the ILS laser is sent to the spectrometer assembly 14, which disperses the output beam with respect to wavelength. In FIG. 1a, diffraction gratings 38 and 40 are employed to disperse the output beam 32 exiting the ILS laser 12 with respect to wavelength. Lenses 34 and 36 expand the output beam 32 prior to incidence on the diffraction gratings 38 and 40. Lens 42 focuses the output of the spectrometer assembly 14 onto the optical detector 16.

In one prior art method, (1) the spectrometer assembly 14 contains a dispersive optical element that can be scanned with respect to wavelength, and (2) the optical detector 16 comprises a single channel detector. FIG. 1a depicts this scanning dispersive optical element as a diffraction grating 38.

The spectral signature of the gaseous species in the laser cavity 24 is obtained by scanning the dispersive optical element (grating 38) while the light transmitted through the spectrometer assembly 14 passes through an appropriate aperture 46 placed in front of the (single channel) optical detector 16. (Aperture 46 may simply comprise a slit.) The intensity of the light transmitted through the spectrometer assembly 14 is measured by the optical detector 16 as diffraction grating 38 is scanned. The optical detector 16 outputs an electrical signal to indicate this intensity. (For example, the electrical signal may be proportional to the ILS laser intensity.) Additionally, the spectrometer sends an electronic signal to the computer 18 that indicates the respective wavelength. In this manner, the computer 18 correlates the intensity determined by the optical detector 16 with the wavelength as determined by the spectrometer assembly 14. Thus, the spectrometer assembly 14 and the optical detector 16 are operated in conjunction with the computer 18 to enable the spectral distribution of the output beam 32 emanating from the ILS laser 12 to be measured.

FIG. 1b schematically illustrates the sort of data obtained from prior art ILS detection methods. Curve 48 represents a typical spectrally dispersed ILS laser output spectrum (or absorption spectrum) obtained by scanning the wavelength and measuring the intensity of the light transmitted through the spectrometer assembly 14. At wavelengths where absorption features are located, the intensity of the ILS laser 12 is attenuated. Arrows 49 indicate six such absorption features. (Curve 50 depicts the spectral distribution of the ILS laser 12 absent any absorbing gaseous species.) The computer 18 can use the absorption spectrum shown in curve 48 to identify the gaseous species. In particular, the absorption spectrum comprising numerous absorption features within the output spectrum of the ILS laser 12 is measured and compared with the known spectral signature of the gaseous species to be monitored. The positions and relative intensities of the specific absorption features of the gaseous species can be utilized to uniquely identify the gaseous species to be detected. The concentration or amount of the intracavity gaseous species within the laser cavity 24 can be determined from the magnitude of the absorption feature(s) found in the absorption spectrum when the magnitudes are previously calibrated with known concentrations.

In an alternative prior art method, (1) the output beam 32 emanating from the ILS laser 12 is passed through a spectrometer having fixed dispersive optical elements (i.e., gratings 38 and 40 are not scanned), and (2) the optical detector 16 comprises a multichannel detector array. The spectral region over which the ILS laser 12 operates is produced by the spectrometer assembly 14 and is displaced spatially across the (multichannel array) optical detector 16. The aperture 46 (if any) that is placed in front of the optical detector 16 is large enough to allow illumination of a plurality of detectors in the detector array such that multiple wavelengths are simultaneously tracked by the multiple detectors in the detector array.

Accordingly, the specific spectral region that is resolved by the spectrometer assembly 14 is simultaneously measured with the (multichannel array) optical detector 16. The computer 18 operates the (multichannel array) optical detector 16 and reads the intensity measured from the multiple detectors therein. Additionally, the spectrometer assembly 14 sends an electronic signal to the computer 18 that indicates the wavelength resolved by the spectrometer assembly 14. The computer 18 is programmed to convert the electronic signals from the (multichannel array) optical detector 16 and the spectrometer assembly 14 into intensity and wavelength, respectively. In this manner, the computer correlates the intensity determined by the optical detector 16 with the wavelength as determined by the spectrometer assembly 14.

Thus, the spectrometer assembly 14 and the (multichannel array) optical detector 16 are operated in conjunction with the computer 18 to measure and record the spectral distribution of the output beam 32 emanating from the ILS laser 12. An absorption signature similar to that shown in FIG. 1b may be produced.

As described above, the spectral signature is used to identify the gaseous species in the laser cavity 24. The computer records the measured absorption bands comprising numerous absorption features or lines within the output spectrum of the ILS laser 12 and compares them with the known spectral signature of the gaseous species to be monitored. The concentration of the intracavity species can be determined from the magnitude of the absorption feature (s) found in the spectral signature once the magnitudes are calibrated using known concentrations.

It will be appreciated, however, that these prior art methods require the computer 18 to effectively generate a plot of intensity versus wavelength by measuring and recording the intensity at a plurality of wavelengths including the wavelengths corresponding to the absorption features as well as the wavelength regions surrounding the absorption features where absorption is minimal.

The method of the present invention, in contrast, is conceptually much simpler than these prior art approaches. Rather than monitoring the distribution of intensities over a plurality of wavelengths, the method of the present invention involves only determining one or more temporal characteristics of the ILS laser 12 during operation, i.e., producing light, within a pre-determined wavelength region. Measuring and recording multiple absorption features within the spectrum of the ILS laser 12 is not necessary.

Prior art approaches rely on measuring laser output intensity as a function of wavelength. The method of the present invention relies on measuring the laser output intensity as a function of time. This measurement is taken with only a single channel detector and no wavelength-selective element (s) between the ILS laser and the detector. Sensitivity limitations in prior art approaches were often given by the dispersive capability of the wavelength-selective optical elements used. In the present invention, these elements are unnecessary. Thus, sensitivity is limited by other factors, e.g. detector temporal bandwidth, timing jitter, and/or gain pumping stability. Technical solutions for reducing these limitations in the present invention are generally available and technological improvements are continually made as a result of significant research efforts by industry. Reducing sensitivity limitations in the prior art approaches is more difficult, since increasing dispersion usually means increasing the size of the instrumentation.

The method of the present invention is conceptually different from the prior art method for ILS gas detection in another respect; namely, the detector 16 used in the present invention has a temporal bandwidth that is related to whatever temporal characteristic is being measured. Prior art methods of ILS detection employ a detector 16 that is either a photodiode array in the case a spectrometer or wavelength-selective element which is fixed in wavelength or a single channel detector used in conjunction with a scanned wavelength-selective optical element. The task of the detector is to measure the intensity of light exiting the ILS laser at a specific wavelength or set of wavelengths determined by the resolving power of the wavelength selective optical element. In prior art methods, the sensitivity, dynamic range, or pixel spacing of the temporal detector were of primary importance. The temporal bandwidth of the detector was not usually critical as long as the detector was fast enough to actually generate a signal in response to the ILS laser output during the measurement period, tens to hundreds of microseconds. A detector with a temporal bandwidth much faster than this measurement range would not lead to higher sensitivity performance of the prior art methods. The high temporal bandwidth would essentially be integrated over the measurement period. In fact, the high temporal bandwidth would be detrimental as it would cause pick-up of higher frequency noise components not related to the ILS signal.

In the present invention, the temporal bandwidth of the detector is of primary importance. The actual temporal bandwidth required depends on the specific temporal phenomena to be measured, the ILS laser configuration, and the ILS laser operational parameters. For example, the time delay between the start of the pumping process and the onset of operation of the ILS laser can vary from less than a microsecond to many milliseconds depending on pumping power, resonator alignment, laser crystal temperature, the presence of an intracavity absorber, etc. An individual photon pulse event, on the other hand, may occur on the order of nanoseconds. A detector capable of measuring the pulse shape would need a temporal bandwidth comparable to the event length and preferably an order of magnitude or more faster. Different ILS lasers will also have different requirements for detector temporal bandwidth, as the temporal phenomena are related to the particular gain properties of the active medium.

The temporal response of a solid state laser to the presence of an intracavity absorber is used to determine the specific concentration of the absorber within a calibrated range. Solid state lasers are subject to well-defined temporal characteristics as a result of the pumping process. A specific example is the presence of relaxation oscillations. These relaxation oscillations are sensitively dependent on the laser cavity gain and loss properties. Thus, the loss introduced by an intracavity absorber will cause a perturbation to the relaxation oscillation temporal profile.

Several features are present as a result of reliance on the temporal characteristic(s) of the ILS laser 12.

For example, no spectrometer or wavelength-selective element is required outside of the ILS laser, as only the profile of the laser in the time domain need be determined. Further, only a single channel detector with a temporal bandwidth capable of resolving the relaxation oscillation period or other temporal characteristic is required. A photodiode array is not necessary. However, a detector with higher temporal bandwidth may be able to measure changes in the lineshape of a single output pulse.

Any feature of the temporal output of the ILS laser that is responsive to a change in the intracavity gaseous species absorption may be used as a source of calibration. These include, but are not limited to:

(1) a delay between the initial pumping of the ILS laser and the onset of laser operation;
(2) at least one of the period and frequency of the relaxation oscillations;
(3) the increase or decrease of the relaxation oscillation period as a function of the number of pulses;
(4) the lifetime of the relaxation oscillation decay in event of an exponential or bi-exponential decay profile;
(5) any change in a fit parameter as the result of fitting all or part of the ILS laser temporal profile to an analytic waveform;
(6) any change in a fit parameter as the result of fitting all or part of the ILS laser temporal profile by a numerical algorithm;
(7) the lineshape of one or more of the individual output pulses;
(8) the response of the temporal profile to a change in an operational parameter while the intracavity gaseous absorber is present; and
(9) a quantifiable increase or decrease in the chaotic nature of the gas detection system in response to the presence of the intracavity gaseous species in the event the ILS laser output is chaotic.

No acousto-optic modulator or temporal laser output control is required in the practice of the present invention, since the entire time-resolved laser profile is obtained by the single channel detector 16.

Intracavity wavelength-selective elements, such as pellicles, birefringent tuners, gratings, and the like may enhance the temporal response of the ILS laser 12 by limiting the ILS laser spectral bandwidth to coincide only with the intracavity gaseous species absorption feature(s), although the system can be operated broadband also. An intracavity wavelength-selective element is shown in phantom at 52 in FIGS. 2 and 3, since it is optional.

The ILS laser 12 may be operated with single or multiple longitudinal modes and single or multiple transverse modes.

A computer 18 is optionally used, depending on the complexity of the data acquisition and analysis. For example, a computer is not necessary to operate a system based on time delay (item 1 above).

The entire laser cavity 24 can function as the gas cell 22 in the event of non-corrosive gases or acceptably slower response times. Alternatively, the intracavity gas cell 22 can be included for faster response times and for corrosive gas compatibility.

Any external conditions that affect the temporal profile of the ILS laser 12 must be either quantified, calibrated, or controlled. For example, the time delay of item 1 above is sensitively dependent on ambient (system) temperature and pump laser power. Other external conditions that affect the temporal profile of the ILS laser 12 include, but are not limited to, pump laser duty cycle, pump laser polarization, length of pump laser pulse, and laser crystal temperature.

The system 10 must be calibrated for a particular set of gaseous sample components, as impurities or unknown gases may result in false positive readings.

Several reasons tend to favor the use of ILS lasers 12 having a spectral bandwidth that is substantially broad relative to the spectral bandwidth of the absorption features produced by the gaseous species. As described above, the various absorption features in the spectral signature aid the computer 18 in identifying the particular gaseous species to be detected. Thus, prior art methods of identifying absorbing gaseous species rely on ILS lasers 12 having a spectral bandwidth that is large enough to include more than one absorption feature. Additionally, an ILS laser 12 having multiple longitudinal modes is most advantageous since the enhanced detection sensitivity of ILS techniques derives mainly from the non-linear gain versus loss competition of a multimode laser. Consequently, prior art methods employ ILS lasers 12 that have a spectral bandwidth that is large enough to include multiple longitudinal modes.

The ILS laser of the present invention, however, will become progressively more sensitive as the spectral bandwidth decreases to less than the absorption bandwidth of the intracavity absorber. The present invention can even operate as a sensor when the spectral bandwidth is reduced to a single longitudinal mode. In the prior art, the sensitivity derives from competition between the oscillating laser modes of a broadband laser in the presence of a narrow band absorber. In the present invention, the temporal characteristics of the laser are dependent on the gain and loss properties of the laser resonator. The temporal characteristics change in the presence of a narrow band intracavity absorber. This change is exacerbated when the loss introduced by the intracavity absorber is a significant fraction of the total resonator loss. Thus, narrow band laser operation directly on the intracavity absorption feature will produce a large change in the ILS laser temporal characteristics when the intracavity absorber is introduced. However, the ILS laser temporal characteristics will still change in response to the presence of the intracavity absorber even in the case of broadband operation. The sensitivity may be reduced somewhat in this case.

The spectral bandwidth ($\Delta v_{laser}$) of the ILS laser 12 is defined by the wavelength region over which the gain medium 20 can operate, the spectral characteristics of the mirrors 26 and 28, and the wavelength regions over which each of the optical elements within the optical cavity 24 are transmitting. In particular, $\Delta v_{laser}$ is defined by the convolution of the spectral bandwidth of the gain medium 20 and the mirrors 26 and 28, as well as the spectral bandwidth of any other separate intracavity optical elements, e.g., pellicle or birefringent tuner within the laser cavity 24.

Consequently, only one or more of the temporal characteristics of the output of the ILS laser 12 need be monitored in order to quantitatively determine the concentration of the absorbing gaseous species when using the ILS method of the present invention.

Figure 2:
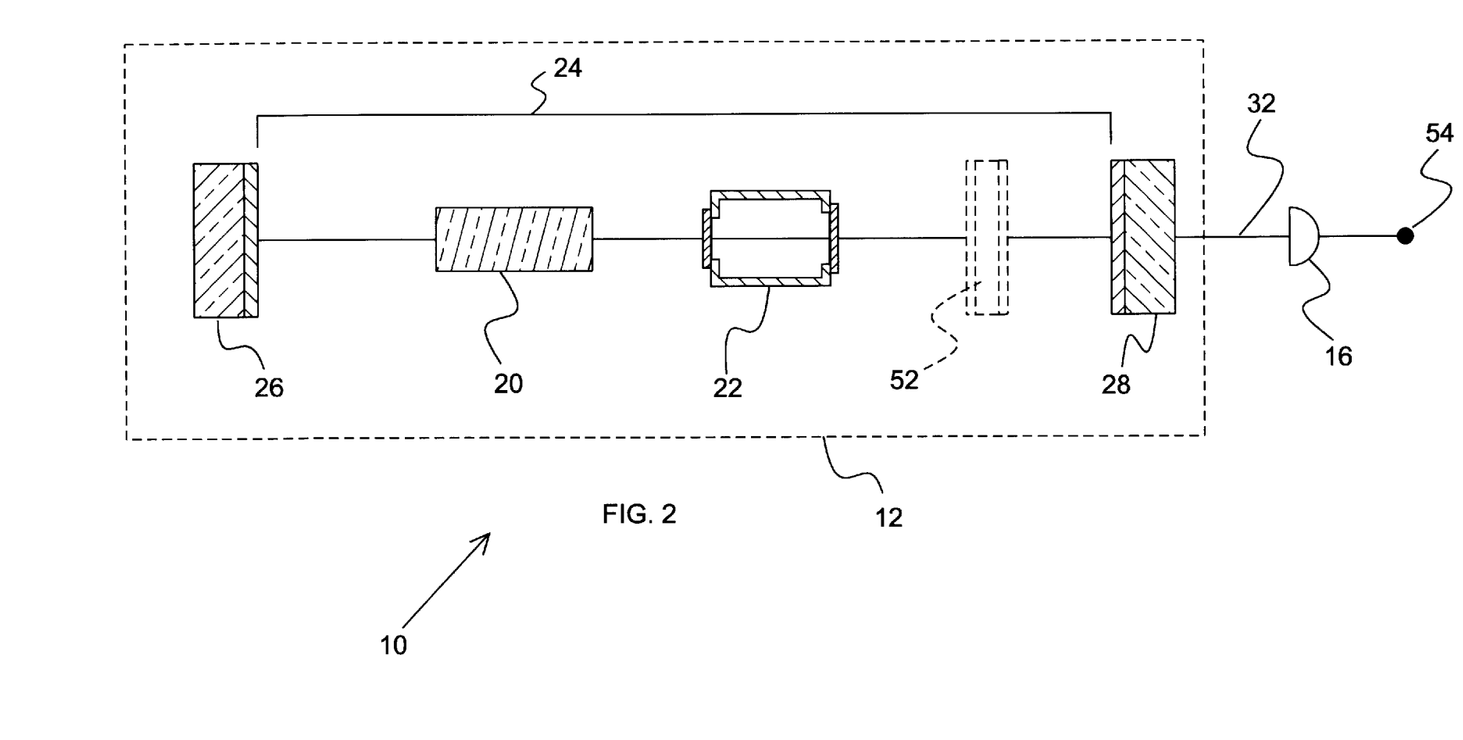
FIG. 2 is a cross-sectional view depicting a gas detection system of the present invention comprising an ILS laser and an optical detector.

FIG. 2 schematically illustrates the method and apparatus of the present invention, which is directed to detecting gaseous species in a gas sample. In particular, FIG. 2 shows a cross-section of an ILS gas detection system 10 constructed in accordance with the present invention.

The ILS gas detection system 10 of the present invention simply comprises an ILS laser 12 and an optical detector 16 with a sufficient temporal bandwidth to measure the ILS laser temporal characteristics.

The ILS laser 12, as depicted in the embodiment of the present invention that is shown in FIG. 2, includes a gain medium 20, a gas sample cell 22, and an optional wavelength-selective optical element 52, all of which are situated within an optical resonator 24 formed between mirrors 26 and 28.

Although the laser cavity 24 shown in FIG. 2 is a linear cavity, it will be appreciated that alternative cavity designs can be employed in accordance with the present invention. One example is three or greater mirror resonators designed for astigmatic compensation. Another example is a traveling wave resonator such as a ring laser.

In the ILS laser shown in FIG. 2, the optional wavelength-selective optical element 52 serves to (1) narrow the spectral bandwidth and (2) tune the wavelength of the ILS laser 12. Preferably, the wavelength-selective optical element 52 is chosen to ensure that the ILS laser 12 has a spectral bandwidth that is not larger than the spectral bandwidth of the overlapped portion of the absorption band. Additionally, the wavelength-selective optical element 52 guarantees that the spectral bandwidth of the ILS laser 12 is tuned to coincide with the absorption band comprising, for example, an absorption feature or a plurality of consecutive absorption features.

The optional wavelength-selective optical element 52 shown in FIG. 2 comprises a metallized pellicle that acts as a thin high-reflectance Fabry-Perot etalon that provides the required narrowband tuning. The metallization increases the finesse of the etalon and narrows the spectral bandwidth thereby creating a narrow-band bandpass filter. Tuning the ILS laser 12 to the appropriate wavelength can be accomplished by rotating the etalon to the angle that passes the desired wavelength. Examples of other wavelength-selective optical elements 52 that may be suitably employed in the present invention include optical bandpass filters, diffraction gratings, prisms, electrooptic bandpass filters, single and multiple plate birefringent filters, and combinations thereof.

It will be appreciated that the potential (or operational) wavelength band of the ILS laser 12 depends on the gain medium 20 and any optical coatings formed on the optical components that are situated within the laser cavity 24 as well as any optical coatings formed on mirrors 26 and 28. Accordingly, instead of introducing a wavelength-selective optical element 52 into the laser cavity 24, the gain medium and any coatings on the optical components that are used in the ILS laser 12, e.g., mirrors 26 and 28, or windows on the gas sample cell 22, or coatings on crystal 20, can be designed to narrow the spectral bandwidth and tune the wavelength of the ILS laser to overlap only the absorption band associated with the gaseous species to be monitored in the manner described above.

For the ILS laser 12 depicted in FIG. 2, however, the potential (or operational) wavelength band of the ILS laser 12, $W_{laser}$, is defined by the convolution of the wavelength band over which the gain medium 20 can operate, the wavelength band over which the mirrors 26 and 28 are reflecting, the wavelength band over which mirror 28 is transmitting, as well as the wavelength band over which any of the other intracavity optical elements (e.g., wavelength-selective optical elements) within the laser cavity 24 are transmitting. It will be further appreciated that ILS laser 12 requires a pumping source (not shown) to drive the ILS at and slightly above its threshold. For example, an optical pumping source may be employed that delivers optical radiation to the gain medium 20. This optical pumping source may take the form of a laser, a laser diode, or a flashlamp. These sources may be used individually or in combination. Use of a multiplicity of like or different pumping sources is contemplated.

FIG. 2 shows that laser light generated within the gain medium 20 is directed to the gas sample cell 22 and passes through the gas sample therein. As described above, gaseous species within the laser cavity 24 and, in particular, within the gas sample cell 22, may introduce absorption losses. Thus, absorption from the intracavity gaseous species will increase the loss in the ILS laser resonator 24 and thereby change the laser temporal characteristics. Therefore, to determine the concentration of the gaseous species, the ILS laser 12 must be calibrated within well-defined operating conditions. The output beam 32 that emanates from the laser is detected directly by an optical detector 16.

In its simplest form, the optical detector 16 comprises a single channel detector such as a photodiode, a photoconductor, or a photomultiplier tube. Other detectors may suitably be employed in the present invention. One requirement for the optical detector 16 is that the detector must be able to sense the ILS laser beam 32 and produce a resultant electrical signal. Accordingly, an electrical output terminal 54 extending from the optical detector 16 is depicted in FIG. 2. Another requirement for the optical detector 16 is that it have a temporal bandwidth sufficient to measure the temporal characteristic of the ILS laser 12 that is being altered by the presence of the gaseous absorber.

The gas detection system 10 of the present invention differs from the prior art system that is shown in FIG. 1a in that no spectrometer assembly 14 nor computer 18 is required. The gas detection system 10 depicted in FIG. 2 also does not require a scanning dispersive optical element, a multichannel detector array, or a slit that is placed in front of the optical detector 16.

Additionally, the gas detection system 10 shown in prior art does not include the optional wavelength-selective optical element 52 within the laser cavity 24 that narrows and tunes the spectral bandwidth of the ILS laser 12 to coincide only with the absorption band associated with the gaseous species to be detected.

It will be appreciated that since ILS offers increased sensitivity beyond prior art methods, weak transitions previously not measured may become measurable for the first time with the gas detection system 10 of the present invention. Knowledge of where to tune the ILS laser 12 must be obtained from spectroscopic studies of the gaseous species of interest that show the spectral location of various absorption features. An understanding of how to optically control the wavelength and spectral bandwidth of the ILS laser 12 is also required to match the spectral output of the laser with the absorption feature (or features).

Additionally, to eliminate the possibility of spectral interferences that could lead to false positive readings, spectroscopic studies are required for any additional gaseous species that are likely to be present in a given gas sample. If such additional gaseous species are not to be detected, the spectral output of the ILS laser 12 must be tuned away from any absorbing feature that is produced by these other gaseous species. Potential contributions from absorption features arising from other gaseous species will then be absent in the wavelength region where the ILS laser 12 emits light. Thus, the operational wavelength of the ILS laser 12 must be chosen (1) to coincide with an absorption feature(s) associated with the gaseous species to be detected and (2) to avoid spectral interference from gaseous species that are not of interest. If the foregoing requirements are satisfied, then the spectral interaction with the ILS laser 12 output will be traceable only to absorption from the gaseous species to be monitored. Accordingly, the change of the ILS laser 12 temporal characteristics, when calibrated, will accurately measure the concentration of the monitored gaseous species.

The identity of the gaseous species is known because the selected spectral region over which the ILS laser 12 operates coincides solely with the absorption band associated with the gaseous species being monitored.

The concentration of the gaseous species is known by calibrating the change in the temporal characteristics of the ILS laser 12 under well-defined operating conditions with a known concentration of gaseous species in the laser cavity 24. This calibration depends on a specific set of operational parameters that includes temperature, pressure, laser gain, pump laser duty cycle, and any other parameter that alters the gain or loss of the ILS laser 12. It will be appreciated that these operational parameters must be held constant to ensure that the gas detection system 10 remains calibrated. Alternatively, varying these operational parameters will change the calibrated sensitivity of the gas detection system, thus enabling multiple calibrations under different well-defined operational conditions to increase the dynamic range of the gas detection system. Regardless, knowledge of the specific operational parameters that affect the temporal characteristics of the ILS laser 12 is required to design a gas detection system 10 that maintains calibration over extended use.

Figure 3:
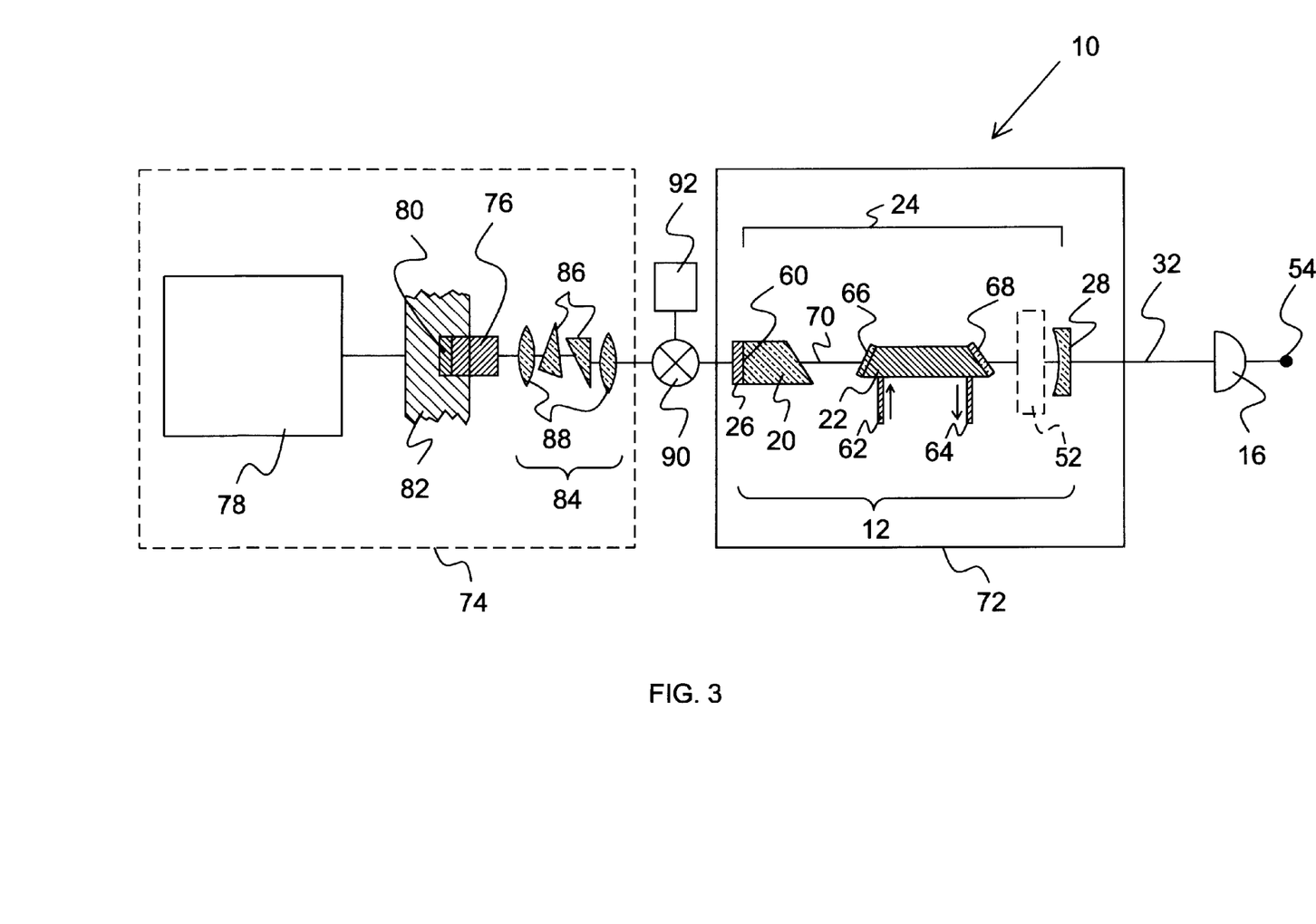
FIG. 3 is a schematic representation of another embodiment of the ILS laser of the present invention.

Referring now to FIG. 3, a separate embodiment of the present invention is shown. In accordance with the present invention, the spectral bandwidth ($\Delta v_{laser}$) of the ILS laser 12 depicted in FIG. 3 is narrow enough to coincide exclusively with an absorption band or region associated with the gaseous species to be monitored. Again, as with FIG. 2, the wavelength-selective optical element 52 is optionally inserted within the laser cavity 24.

As discussed above, the term "absorption band" is defined as a single uninterrupted wavelength region in the absorption spectrum wherein absorption occurs at each wavelength. Accordingly, if an absorption spectrum contains two absorption lines, $A_1$ and $A_2$, separated by region, B, where no absorption is observed, then two absorbing lines, $A_1$ and $A_2$, correspond to separate absorption bands. If, however, the two absorption lines, $A_1$ and $A_2$, are only separated by a local absorption minimum (or local maximum in intensity), then the two absorbing lines, $A_1$ and $A_2$, correspond to a single absorption band.

In accordance with the present invention, the gas detection system 10 depicted in FIG. 3 comprises an ILS laser 12 and an optical detector 16. The ILS laser 12 includes a gain medium 20 that is located within the laser cavity 24 defined by mirrors 26 and 28. The laser cavity 24 is a linear cavity and the gain medium 20 comprises an ion-doped crystal. The first mirror 26 is formed by depositing a reflective coating on one end 60 of the ion-doped crystal. The second mirror 28 comprises a curved reflector.

Although the laser cavity 24 shown in FIG. 3 is a linear cavity, it will be appreciated that alternative cavity designs can be employed in accordance with the present invention, as listed above.

In the practice of the present invention, an ion-doped crystal is used as the gain medium 20 crystal. It will be appreciated that any ion-doped crystal may be employed as is suited to the particular use contemplated. Accordingly, it is not intended that the ion-doped crystals specifically disclosed herein, including those listed below, are to be exhaustive.

A sampling of ion-doped crystals that can be suitably employed in the method and apparatus of the present invention include $Tm^{3+},Tb^{3+}$:YLF, Cr:Tm:Ho:YAG, $Cr^{4+}$:YSO, $Cr^{4+}$:YAG, $Cr^{4+}$:YSAG, $Er^{3+}$:GSGG, $ER^{3+}$:YSAG $Er^{3+}$:YLF, $Er^{3+}$:$Yb^{3+}$:glass, $Ho^{3+}$:YSGG, $Ho^{3+}$:$Tm^{3+}$:LUAG, $Tm^{3+}$:$Ho^{3+}$:YLF, $Tm^{3+}$:$Ho^{3+}$:YAG, $Tm^{3+}$:Ca Y SOAP, $Tm^{3+}$:YLF, $Tm^{3+}$:glass, $Tm^{3+}$:Ca La SOAP, $Tm^{3+}$:YOS, $Tm^{3+}$:YSGG, $Tm^{3+}$:YAG, $Tm^{3+}$:$YVO_4$, $Yb^{3+}$:YAG, Cr:Forsterite, Er:Yb:Glass, $CO_2$:$MgF_2$, $Cr^{2+}$:ZnSe, and $Cr^{2+}$:ZnS/ZnSe/ZnTe. Other materials, whether gas, liquid, or solid, may also be used as the gain medium 20.

FIG. 3 additionally shows a gas sample cell 22 located within the laser cavity 24. The gas sample cell 22 isolates the gas sample from the laser components. It will be appreciated that the gas sample cell 22 is not required for gas samples that are non-corrosive, in which case, the gas sample may be contained within the entire laser cavity 24.

The gas sample cell 22 is provided with an inlet conduit 62 and an outlet conduit 64. Respective cell windows 66 and 68 are mounted on the distal ends of the gas sample cell 22 and permit beam 70 to pass through the gas sample to be analyzed. Windows 66 and 68 also seal the gas sample cell 22.

In the event that gas sample cell 22 is present within chamber 72 containing the ILS laser 12, it is necessary that the gaseous species that are to be detected are removed or eliminated from the chamber. By removing the gaseous species from the chamber 72, the system response obtained through use of the gas detection system 10 accurately indicates the presence and amount of the gaseous species contained within the gas sample cell 22. After purging or evacuating the chamber 72 of gaseous species, the gas sample is fed into the gas sample cell 22 through inlet conduit 62 and outlet conduit 64 (for example, when the gas sample comprises corrosive gas). However, in such cases where the gas sample does not chemically react with the laser components, the gas sample may be communicated into the chamber 72.

As discussed above, the ILS laser 12 requires a pumping source 74 to excite the gain medium 20. Optical excitation of the ion-doped crystal gain medium 20 is provided by the pumping source 74, which comprises a semiconductor diode laser 76.

It should be appreciated that pumping source 74 may comprise any suitable optical pumping source, either coherent or incoherent, continuous or pulsed, that will drive the ILS laser 12. For example, pumping source 74 may alternatively comprise a solid state crystal laser (e.g., Nd:YAG), a gas laser, one or more flashlamps, fiber laser, or any other pumping source that is suitable for pumping the ILS laser 12.

FIG. 3 shows the semiconductor diode laser 76 being powered by an electrical power supply 78 and being cooled by a thermoelectric cooler 80. The semiconductor laser diode 76 and the thermoelectric cooler 80 are mounted in a heatsink 82 provided to dissipate heat generated by the semiconductor diode laser.

Use of a semiconductor diode laser 76 as a pumping source 74, however, typically requires use of a beam shaping optics 84 to facilitate optical matching between the semiconductor diode laser 76 output and the ILS laser 12. Examples of beam modification optics include diffractive optics, refractive optics, gradient index optics wherein the refractive index varies axially, gradient index optics wherein the refractive index varies radially, micro-optics, and combinations thereof. FIG. 3 shows the beam shaping optics 84 comprising macroscopic optics, which include a pair of anamorphic prisms 86 and a pair of lenses 88. Alternatively, a beam expanding telescope or micro-optics that are placed within several micrometers of the semiconductor diode laser 76 may be employed.

FIG. 3 further shows a first modulator 90 inserted between the beam shaping optics 84 and the gain medium 20. The first modulator 90 is powered and controlled by a modulator driver 92. The first modulator 90 alternatively attenuates and transmits the pumping beam 96 emanating from the semiconductor diode laser 76 and thereby periodically prevents the pumping beam from pumping the gain medium 20. In this manner, the first modulator 90 causes the pumping beam 96 to reproducibly pump the gain medium 20 such that the ILS laser 12 will be switched on and off.

It will be appreciated that interruption in pumping can be achieved utilizing a variety of means, including, but not limited to using a mechanically operated chopper, an electro-optic or acousto-optic modulator, and a shutter. Alternatively, the electrical power supplied to the pumping source 74 (e.g., semiconductor diode laser 76) can be varied, thereby causing the output of the semiconductor diode laser to fluctuate between high and low intensity levels that periodically bring the gain medium 20 just above and below the threshold required for laser operation.

FIG. 3 depicts the output beam 32 from the ILS laser 12 being directed to the optical detector 16. It will be appreciated that the light output from the ILS laser 12 can alternatively be transmitted via an optical fiber link, i.e., an optical fiber or an optical fiber bundle, to a remote site where the optical detector 16 is located.

The optical detector 16 is chosen to have a temporal bandwidth sufficient to resolve the particular temporal characteristic of ILS laser 12 being used for calibration. The detector may be capable of obtaining the entire temporally resolved output of ILS laser 12.

Figure 4:
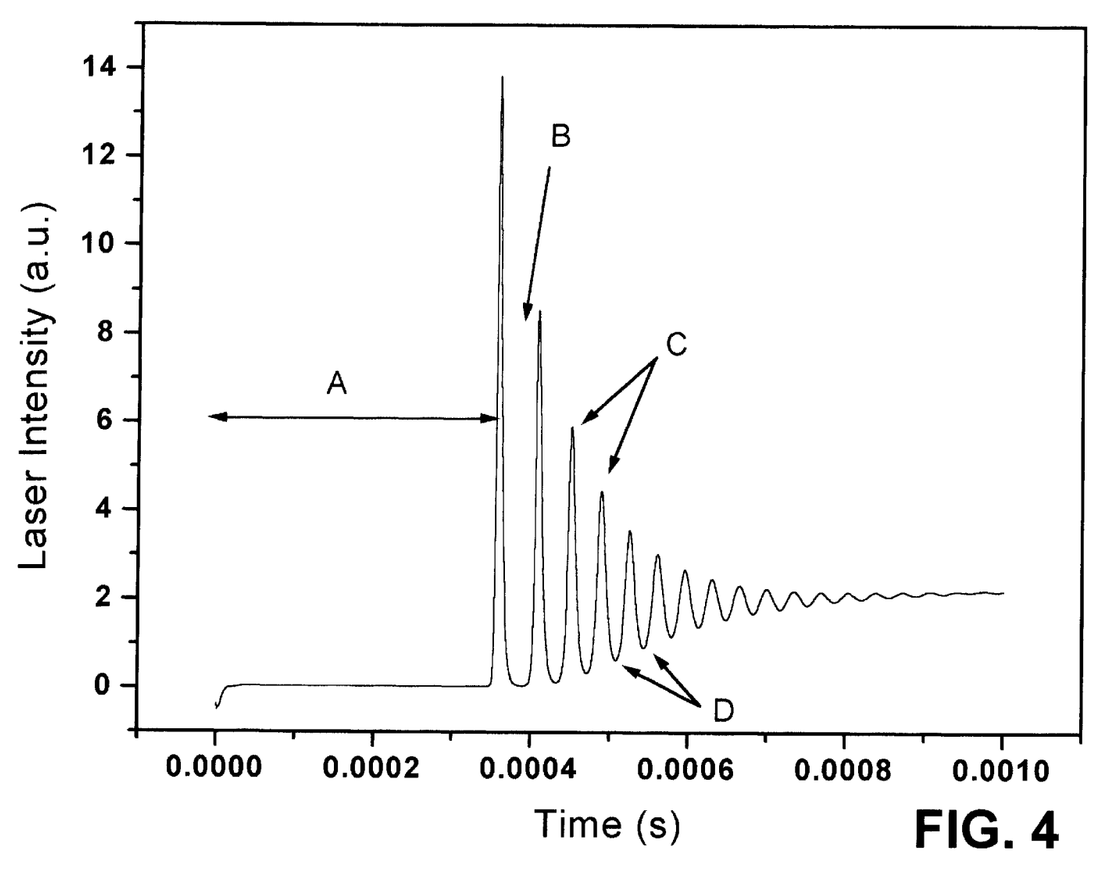
FIG. 4, on coordinates of intensity and time, is a plot of the temporally resolved output of the ILS laser of the present invention showing the oscillatory nature of the temporal output of the ILS laser.

FIG. 4 shows the output of an ILS laser using a detector with sufficient temporal bandwidth to resolve the temporal characteristics of the laser output. The ILS laser in this case employed a semiconductor diode laser pumping a $Tm^{3+}$:YAG crystal. As described above, the pump laser radiation was switched alternately on and off.

The temporal characteristics of the present system follow a well-known laser phenomenon known as relaxation oscillation. These relaxation oscillations are caused by the solid state laser responding to a non-equilibrium laser population inversion. They come about as the laser attempts to reach an equilibrium inversion in response to a rapid up-pumping rate. Several characteristics of the laser temporal output are evident that depend on the resonator gain and loss, as shown in FIG. 4: (1) There is a significant time delay between the start of optical pumping, which begins at zero time, and the onset of the ILS laser operation, denoted A. (2) There is a time delay between successive pulses of the ILS laser, denoted B. (3) There is a decrease in the amplitude of successive laser output pulses, denoted C. (4) There is an increase in the laser baseline output between successive laser output pulses, denoted D.

It is important to note that oscillatory relaxation is a specific example of a set of temporal characteristics as contemplated by the present invention. Other characteristics, such as the time delay mentioned above for the onset of ILS laser operation, may be present even for laser systems that do not have measurable relaxation oscillations.

The temporal characteristics that are described are dependent on the ILS laser resonator gain and loss. For example, all other parameters being equal, an ILS laser that is pumped at a higher rate will have a shorter delay before onset of laser operation. Other temporal characteristics will also change with pumping rate, crystal temperature, system temperature, pumping duty cycle, etc. Since these temporal characteristics are dependent both on laser gain and loss an increase in loss, such as that introduced by the presence of an intracavity absorber, will cause a change in these temporal characteristics. In addition, increasing loss will result in more significant change in the temporal characteristics. Thus, the change will be dependent on the amount of intracavity absorption which is dependent on the concentration of the absorber. This leads to an ability to calibrate the concentration based on the specific change of one or more temporal characteristics to a known concentration of the absorber.

Figure 5:
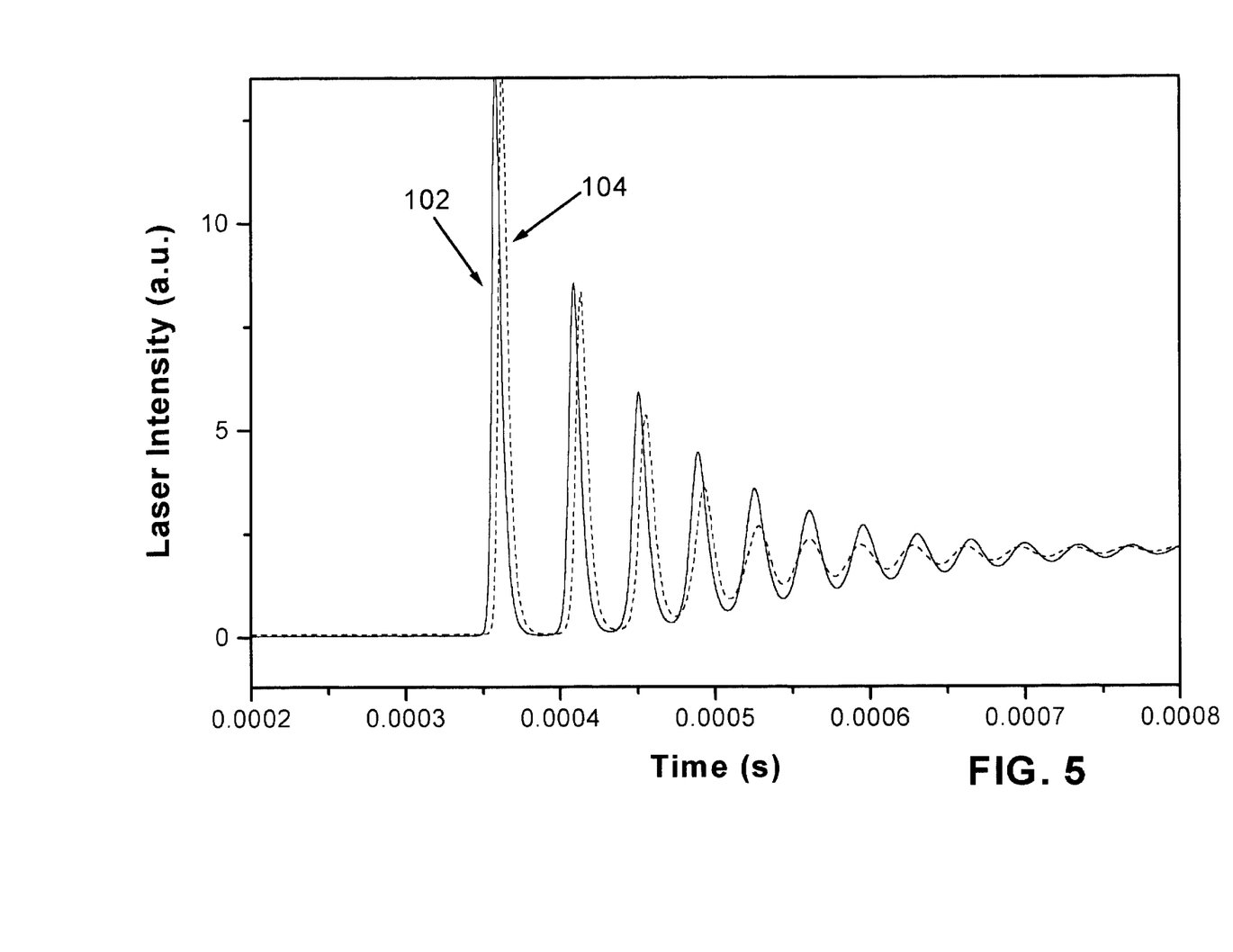
FIG. 5, on coordinates of intensity and time, is a plot of the temporally resolved output of the ILS laser of the present invention for the instances where the absorbing gaseous species within the laser cavity is (i) not present and (ii) present at a detectable level.

A plot of the laser intensity versus time (in seconds) is shown in FIG. 5 for the cases where an intracavity absorber is absent and present. The intracavity absorber in this example was carbon dioxide. FIG. 5 demonstrates how the temporal characteristics of the light output from the ILS laser 12 changes with the presence of carbon dioxide.

Curve 102, based on experimental data, illustrates a series of pulses from ILS laser 12 as it experiences relaxation oscillations. There is no carbon dioxide present in this instance.

Curve 104, also based on experimental data, shows that the presence of carbon dioxide, here 1% vol., in nitrogen changes the temporal characteristics of the relaxation oscillations. The amplitude of corresponding pulses in the two cases is reduced in the presence of carbon dioxide. Additionally, the onset of ILS laser operation is delayed in the presence of carbon dioxide relative to the case where carbon dioxide is absent. Finally, the rate of decay to the limiting value amplitude is faster in the presence of carbon dioxide. All of these parameters change as a result of the increased loss in the ILS laser resonator due to intracavity absorption by carbon dioxide. The loss introduced by the absorption is proportional to the concentration of the absorber, carbon dioxide. Thus, increased concentration results in increased loss and thereby greater change in the measured temporal characteristics.

Figure 6:
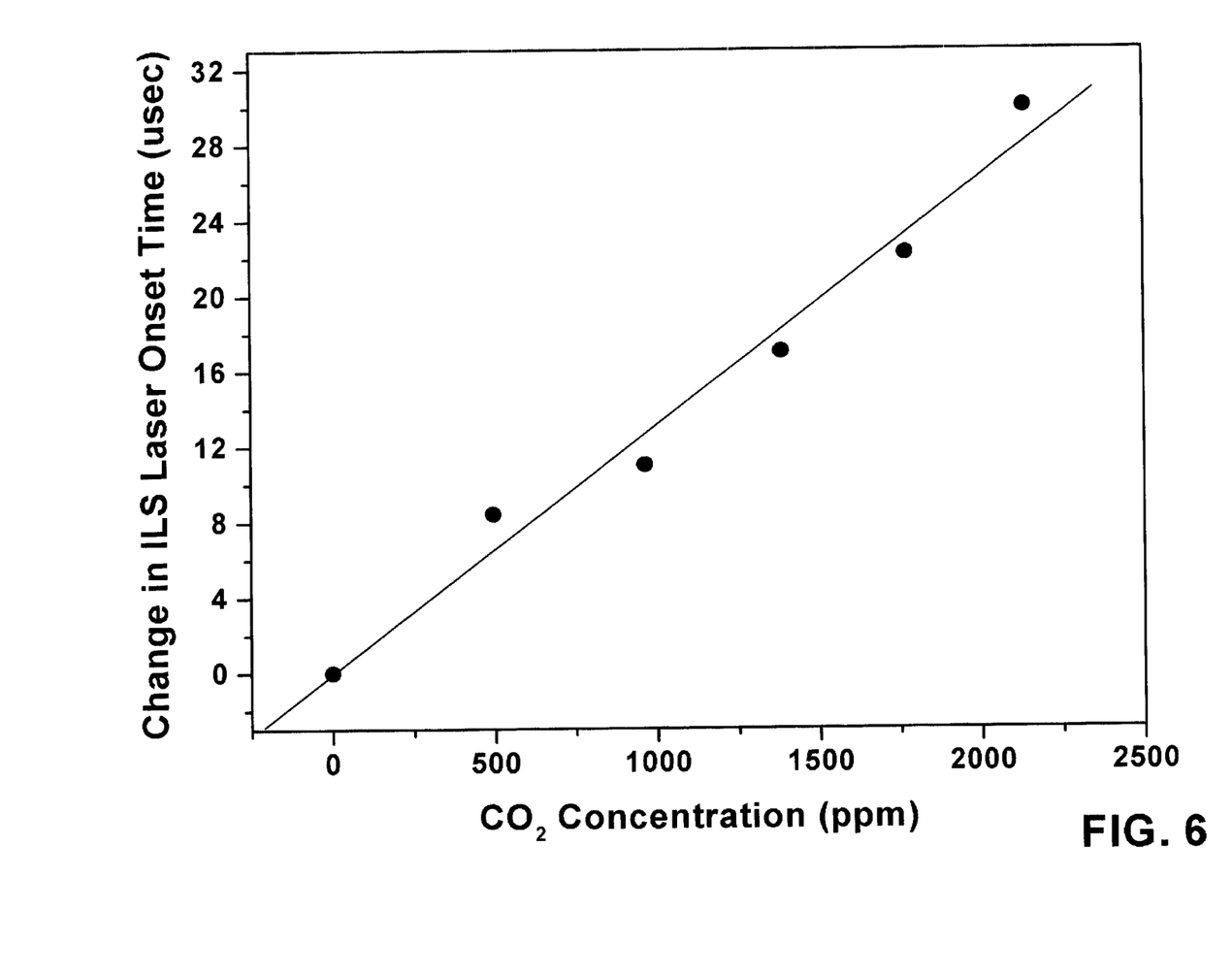
FIG. 6, on coordinates of time (in microseconds) and concentration (in parts per million), is a plot of the change in ILS laser onset time as a function of concentration of an absorber gas, here, $CO_2$.

FIG. 6 illustrates the dependence of the change in ILS laser onset time (in microseconds) on concentration of a gaseous species, here, carbon dioxide in nitrogen. In this connection, the method and apparatus of the present invention may be used in the analysis of any gaseous species.

Thus, when the spectral bandwidth, $\Delta v_{laser}$, of the ILS laser 12 is comparable to the spectral bandwidth, $\Delta v_{laser}$, of the overlapped portion of the absorption band assigned to the intracavity gaseous species being monitored, the method and apparatus of the present invention can be utilized to measure the concentration of the gaseous species by measuring one or more temporal characteristics of the ILS laser. The identity of the gas species detected has been determined by the spectral overlap of the ILS laser wavelength with the absorption feature(s).

Utilization of the method of the present invention results in an ILS gas detection system 10 that is substantially smaller, simpler, less expensive, and easier to use than prior art ILS sensors that rely on mapping the wavelength distribution of the output of the ILS laser 12. As a consequence of its smaller size, lower cost, and operational simplicity, the gas detection system 10 of the present invention can be directed to a completely distinct set of applications in gas detection.

Thus, a method and apparatus has been disclosed for detecting the presence of a specific concentration of gaseous species within a calibrated range. It will be readily apparent to those skilled in this art that various modifications may be made in the design and arrangement of the elements set forth herein without departing from the scope of the invention as expressed in the appended claims. Moreover, the application of gas detection system 10, as well as the location of the ILS gas detector, e.g., in a semiconductor fabrication assembly, can vary as may be desired. For example, the specific placement of the various elements within the ILS chamber 72 and gas detector system 10 itself may be modified so long as their configuration and placement suitably enables optical excitation of ILS laser 12 in a readily reproducible manner. These and other modifications in the design, arrangement, and application of the present invention as now known or hereafter devised by those skilled in the art are contemplated by the appended claims.

What is claimed is:

1. A gas detection system for detecting the presence of a specific concentration of gaseous species in a gas sample within a calibrated range, said gaseous species absorbing light within at least one single band of consecutive wavelengths, said system comprising:
  (a) an ILS laser comprising:
     (i) a laser cavity; and
     (ii) a gain medium,
  said ILS laser having at least one measurable temporal characteristic where said gaseous species is absorbing and said absorption induced by said gaseous species is large enough to measurably change the temporal characteristic of the laser within a calibrated range;
  (b) a container for containing said gas sample in said laser cavity, said container allowing an output beam emanating from said gain medium to pass through said gas sample prior to exiting said laser cavity; and
  (c) a detector having a temporal bandwidth sufficient to measure said temporal characteristic.

2. The gas detection system of claim 1 wherein said detector is a single channel detector.

3. The gas detection system of claim 1 wherein said ILS laser comprises components that prevent said ILS laser from operating only at wavelengths outside said band where said gaseous species is absorbing.

4. The gas detection system of claim 3 wherein a wavelength-selective optical element is located within said laser cavity, said wavelength selective optical element preventing said ILS laser from operating only at wavelengths outside said band where said gaseous species is absorbing.

5. The gas detection system of claim 4 wherein said wavelength selective optical element comprises an intracavity optical element selected from the group consisting of a metallized pellicle that acts as a high-reflectance Fabry-Perot etalon that provides narrow-band tuning, an optical bandpass filter, a diffraction grating, a prism, an electro-optical bandpass filter, a single or multiple plate birefringent filter, and combinations thereof.

6. The gas detection system of claim 3 wherein said gain medium has a spectral bandwidth that is narrow enough to prevent said ILS laser from operating only at wavelengths outside said band where said gaseous species is absorbing or has an optical coating thereon that prevents said ILS laser from operating only at wavelengths outside said band where said gaseous species is absorbing.

7. The gas detection system of claim 3 wherein said container comprises a gas sample cell located within said laser cavity, said gas sample cell having windows that allow said output beam from said gain medium to pass through said gas sample, at least one of said windows having an optical coating thereon that prevents said ILS laser from operating only at wavelengths outside said band where said gaseous species is absorbing.

8. The gas detection system of claim 3 wherein said laser cavity is formed from at least two mirrors and at least one of said mirrors has an optical coating thereon that prevents said ILS laser from operating only at wavelengths outside said band where said gaseous species is absorbing.

9. The gas detection system of claim 1 wherein an optical pumping source delivers optical radiation to said gain medium to thereby drive said ILS laser.

10. The gas detection system of claim 1 wherein said band where said gaseous species is absorbing comprises at least one absorption feature and said ILS laser has a spectral bandwidth that is wide enough to at least partially overlap said at least one absorption feature.

11. The gas detection system of claim 1 wherein said measurable temporal response is selected from the group consisting of (1) a delay between an initial pumping of the ILS laser and onset of laser operation; (2) at least one of period and frequency of relaxation oscillations of the ILS laser; (3) an increase or decrease of relaxation oscillation period as a function of the number of pulses; (4) lifetime of a relaxation oscillation decay in event of an exponential or bi-exponential decay profile; (5) any change in a fit parameter resulting from fitting all or part of the ILS laser's temporal profile to an analytic or consistent waveform; (6) any change in a fit parameter resulting from fitting all or part of the ILS laser's temporal profile by a numerical algorithm; (7) lineshape of one or more of the output pulses; (8) response of the ILS laser's temporal profile to a change in an operational parameter while the intracavity gaseous absorber is present; and (9) a quantifiable increase or decrease in chaotic nature of the gas detection system in response to the presence of the intracavity gaseous species in case the ILS laser's output is chaotic.

12. The gas detection system of claim 11 wherein the operational parameter of part (8) is selected from the group consisting of pump laser power, pump laser duty cycle, pump laser polarization, length of pump laser pulse, laser crystal temperature, and system temperature.

13. A method for detecting the presence of a specific concentration of gaseous species in a gas sample within a calibrated range employing an ILS laser, said method comprising:
  (a) determining that said ILS laser has at least one measurable temporal characteristic where said gaseous species absorbs light and said absorption induced by said gaseous species is large enough to measurably change the temporal characteristics of the laser within the calibrated range;

(b) providing said ILS laser comprising:
  (i) a laser cavity; and
  (ii) a gain medium,
wherein said ILS laser has said at least one measurable temporal characteristic;

(c) situating said gain medium such that an output beam from said gain medium is directed through said gas sample that is contained in said laser cavity prior to exiting said laser cavity; and (d) situating a detector having a temporal bandwidth sufficient to detect said at least one temporal characteristic so as to detect the change in the temporal characteristic of the laser.

14. The method of claim 13 wherein said detector is a single channel detector.

15. The method of claim 13 wherein said ILS laser includes components therein that prevent said ILS laser from operating only at wavelengths outside said band where said gaseous species is absorbing.

16. The method of claim 15 wherein step (b) includes inserting in said ILS laser a wavelength selective optical element that prevents said ILS laser from operating only at wavelengths outside said band where said gaseous species is absorbing.

17. The method of claim 16 wherein said wavelength-selective optical element comprises an intracavity optical element selected from the group consisting of a metallized pellicle that acts as a high-reflectance Fabry-Perot etalon that provides narrow-band tuning, an optical bandpass filter, a diffraction grating, a prism, an electro-optical bandpass filter, a single or multiple plate birefringent filter, and combinations thereof.

18. The method of claim 15 wherein said gain medium has a spectral bandwidth that is narrow enough to prevent said ILS laser from operating only at wavelengths outside said band where said gaseous species is absorbing or has an optical coating thereon that prevents said ILS laser from operating at wavelengths outside said band where said gaseous species is absorbing.

19. The method of claim 15 additionally comprising inserting a gas sample cell within said laser cavity, said gas sample cell having windows that allow said output beam from said gain medium to pass through said gas sample, at least one of said windows having an optical coating thereon that prevents said ILS laser from operating only at wavelengths outside said band where said gaseous species is absorbing.

20. The method of claim 15 additionally comprising forming said laser cavity from at least two mirrors wherein at least one of said mirrors has an optical coating thereon that prevents said ILS laser from operating only at wavelengths outside said bands where said gaseous species is absorbing.

21. The method of claim 13 additionally comprising driving said ILS laser with a pumping source comprising an optical pumping source that delivers optical radiation to said gain medium.

22. The method of claim 13 wherein said band where said gaseous species is absorbing comprises at least one absorption feature and said ILS laser has a spectral bandwidth that is wide enough to at least partially overlap said at least one absorption feature.

23. The method of claim 13 wherein said measurable temporal response is selected from the group consisting of (1) a delay between an initial pumping of the ILS laser and onset of laser operation; (2) at least one of period and frequency of relaxation oscillations of the ILS laser; (3) an increase or decrease of relaxation oscillation period as a function of the number of pulses; (4) lifetime of a relaxation oscillation decay in event of an exponential or bi-exponential decay profile; (5) any change in a fit parameter resulting from fitting all or part of the ILS laser's temporal profile to an analytic or consistent waveform; (6) any change in a fit parameter resulting from fitting all or part of the ILS laser's temporal profile by a numerical algorithm; (7) line-shape of one or more of the output pulses; (8) response of the ILS laser's temporal profile to a change in an operational parameter while the intracavity gaseous absorber is present; and (9) a quantifiable increase or decrease in chaotic nature of the gas detection system in response to the presence of the intracavity gaseous species in case the ILS laser's output is chaotic.

24. The method of claim 23 wherein the operational parameter of part (8) is selected from the group consisting of pump laser power, pump laser duty cycle, pump laser polarization, length of pump laser pulse, laser crystal temperature, and system temperature.

* * * * *